United States Patent [19]

Bergeron et al.

[11] Patent Number: 4,724,050

[45] Date of Patent: Feb. 9, 1988

[54] PRETREATMENT OF ION EXCHANGE MEMBRANE

[75] Inventors: Sheryl M. Bergeron; Duane K. Wolcott, both of Baton Rouge, La.

[73] Assignee: The Dow Chemical Company, Midland, Mich.

[21] Appl. No.: 24,960

[22] Filed: Mar. 12, 1987

[51] Int. Cl.$^4$ .......................................... B01D 59/40
[52] U.S. Cl. ................................. 204/1 T; 204/131; 204/98; 204/128; 204/296
[58] Field of Search ................. 204/296, 98, 128, 131, 204/1 T

[56] References Cited

U.S. PATENT DOCUMENTS

| | | | |
|---|---|---|---|
| 3,180,814 | 4/1965 | Kollsman | 204/131 |
| 3,985,631 | 10/1976 | Hora et al. | 204/98 |
| 4,118,308 | 10/1978 | Specht | 204/296 |
| 4,333,810 | 6/1982 | Wolcott et al. | 204/195 |
| 4,586,992 | 5/1986 | Miyake et al. | 204/296 |

Primary Examiner—R. L. Andrews
Attorney, Agent, or Firm—Timothy S. Stevens

[57] ABSTRACT

A method for electrolytically pretreating a cation exchange membrane by partitioning a first aqueous electrolyte solution from a second aqueous electrolyte solution with the membrane and then passing an electrical current through the system so that the cations of the first solution electro-migrate through the membrane into the second solution. The cation composition of the first solution being more than 99.99% of hydrogen ion and a single cation moiety selected from the group consisting of alkali metal cations and alkaline earth cations, the cation composition of the second solution consisting essentially of the same cation composition as the first solution. The result is a membrane that is almost completely equilibrated with the cations of the first solution. The pretreated membrane is especially suitable for use in the sensor for chemical analysis described in U.S. Pat. No. 4,333,810.

9 Claims, 1 Drawing Figure

PRETREATMENT OF ION EXCHANGE MEMBRANE

FIELD OF THE INVENTION

The invention is in the field of pretreatment of cation exchange membranes and specifically to a pretreatment involving the passage of electrical current transporting cationic species through the membrane.

BACKGROUND OF THE INVENTION

Ion Exchange membranes are an important development of modern technology and are used for example in chlor alkali production and in sensors for chemical analysis. One problem with the use of ion exchange membranes is when a new membrane is used in an application, its performance can be poor until it has a chance to equilibrate in the system, e.g., be thoroughly converted to the hydrated cation form of the application. For example, the cation exchange membrane used in chlor alkali cells can fail to pass significant amounts of electrical current until equilibration has occurred to the hydrated sodium ion form of the membrane. U.S. Pat. No. 3,985,631 to Hora et al teaches a chemical pretreatment for chlor alkali cation exchange membrane that results in the introduction of hydrated alkali metal ions substantially throughout the membrane. U.S. Pat. No. 4,333,810 to Wolcott et al teaches preconditioning the cation exchange membrane of a sensor for chemical analysis by exposure to a high concentration of the analyte. The above mentioned patents are fully incorporated herein by reference.

Despite the generally good effectiveness of the preconditioning taught by Wolcott et al, the present inventors noted that the sensor's response was not completely stable until the sensor had been in use for many months.

The present invention is an electrolytic method for the pretreatment of a cation exchange membrane so that the membrane's performance is more stable in use.

SUMMARY OF THE INVENTION

The invention is a method for pretreating a cation exchange membrane comprising two steps. The first step is to partition a first aqueous electrolyte solution from a second aqueous electrolyte solution with the membrane. The cation composition of the first solution being more than 99.99% of hydrogen ion and a single cation moiety selected from the group consisting of alkali metal cations and alkali earth cations. The cation composition of the second solution consisting essentially of the same cation composition as the first solution. The second step is to pass an electrical current sequentially through the first solution, through the membrane, and then through the second solution so that the membrane is essentially completely converted to the cation form of the first solution. The invention can alternatively include the additional subsequent step of installing the pretreated membrane in a sensor for chemical analysis such as the sensor of U.S. Pat. No. 4,333,810.

DETAILED DESCRIPTION OF THE INVENTION

Figure 1:
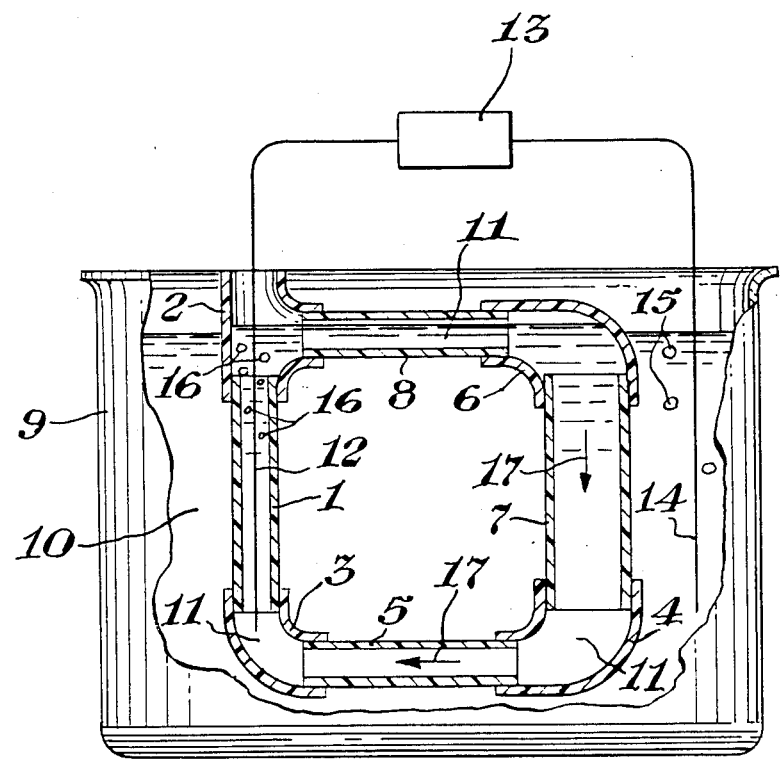
FIG. 1 is a cross-sectional view of a typical apparatus used to carry out the method of the invention.

The present invention is a method for electrolytically pretreating a cation exchange membrane. The specific membrane treated is not critical and it is believed that almost any cation exchange membrane can be beneficially pretreated by the method of the present invention. Preferably, the membrane is "Nafion" cation exchange membrane sold by E. I. duPont de Nemours and Company, Incorporated. More preferably, the Nafion membrane is in the form of a tube. Most preferably, the tubular Nafion is installed in the sensor for chemical analysis described in U.S. Pat. No. 4,333,810.

Referring to FIG. 1 therein is shown a cross-sectional view of a typical apparatus for carrying out the method of the invention. Nafion 810-X tubular cation exchange membrane 1 having an outside diameter of about ¼ inch is connected to a ¼ × ¼ × ¼ inch tubing tee 2 at one end of the membrane 1 and to a ¼ × ¼ inch tubing elbow 3 at the other end of the membrane 1. The elbow 3 is connected to a ¼ × ¼ inch tubing elbow 4 by means of a ¼ inch tubing 5.

The elbow 4 is connected to another ¼ × ¼ inch tubing elbow 6 by means of a ¼ inch tubing 7. The elbow 6 and the tee 2 are connected by ¼ inch tubing 8. A reservoir 9 is provided to contain an aqueous electrolyte solution 10, the cations of which are selected from the group consisting of hydrogen cations, alkali metal cations and alkaline earth cations such as would result from dissolving calcium chloride or lithium chloride in water. Preferably, the reservoir 9, the tubing 5, 7, and 8, the elbows 3, 4, and 6, and the tee 2 are made of Teflon or other nonelectrically conducting plastic.

The tubing 5, 7, and 8, the elbows 3, 4, and 6, and the tee 2 define a generally doughnut shaped interior space 11 that contains an aqueous electrolyte solution, the cation composition of which is more than 99.99% hydrogen ion and a single cation moiety selected from the group consisting of alkali metal cations and alkaline earth cations such as would result from dissolving a highly purified grade of calcium chloride or lithium chloride in deionized water or dilute aqueous acid. Most preferably, the hydrogen ion concentration is as low as possible with any hydrogen ions resulting from, for example, hydrolysis of the electrolyte during the preparation of the solution in the space 11. This solution should fill the space 11 including at least a portion of the tube 8. The cation composition of the solution 10 consists essentially of the same cation composition as the first solution, i.e., if a 99.999% grade of lithium chloride is used to prepare the solution in the space 11, then 99% lithium chloride can be used to prepare the solution 10. Reagent grade lithium chloride is typically about 99% pure. Alfa Products Division of Morton Thiokol Inc., Danvers, MA sells a 99.999% pure grade of lithium chloride.

A negatively charged electrode 12 is connected to a direct current power supply 13 which in turn is connected to a positively charged electrode 14. Preferably, the electrodes 12 and 14 are platinum electrodes which are corrosion resistant in the method of the invention. The power supply 13 imposes a direct current voltage to the electrodes 12 and 14 with the electrode 14 being positive and the electrode 12 being negative. The exact voltage is not critical and generally ranges from about 1 to about 12 volts. The cations in the solution in the space 11 electro-migrate through the membrane 1 to the electrode 14 where they can react to produce hydrogen gas bubbles 15. The direction of the electro-migration of the cations in the space 11 also defines the direction of the passage of electrical current through the membrane 1 in the lexicon of this disclosure. The anions in the solution in the space 11 electro-migrate to the electrode 12 where they can react to form chlorine or oxygen bubbles 16. The electro-migration of cations through the membrane 1 is believed to efficiently and almost completely convert the membrane 1 to the cation form of the solution contained in the space 11 and to almost completely remove from the membrane unwanted and interfering trace level impurity cations such as cations of transition metals. The completeness of the conversion of the membrane 1 to the cation form of the solution in the space 11 requires that the solution in the space 11 be very pure with regard to cation composition. The purity of the cation composition of the solution 10 is less critical because of the direction of cation migration through the membrane. Preferably, the solution 10 is prepared using chemicals that meet the American Chemical Society's standards for "reagent grade" chemicals.

The amount of gas 16 produced at the electrode 12 is regulated by the voltage applied by the power supply 13. The gas 16 tends to recirculate the solution of ultra pure salt contained in the space 11 in the direction of the arrows 17 which helps maintain contact of this solution with the membrane 1. The amount of gas 16 produced should not be so great that the solution in the space 11 "boils" out of the tee 2 nor so low that the flow of current between the electrodes effectively stops. It may be necessary to add more solution to the space 11 during operation of the system. The length of time needed to complete the treatment of the membrane 1 is determined by experimentation and can take as long as a day or more for Nafion 810-X treated for use in the sensor of U.S. Pat. No 4,333,810 when the applied voltage is about 3 volts.

Most preferably, the concentration of electrolyte in the solution contained in the space 11 is between 10% and the solubility limit of the electrolyte in the solution. However, more dilute solutions can be used. Similarly, the most preferred concentration of the electrolyte solution 10 is between 10% and the solubility limit of the electrolyte in the solution but can be more dilute than 10%.

COMPARATIVE EXAMPLE

A 1 inch long section of Nafion 810-X ion exchange tubing, supra, is immersed into 50 ml of a saturated solution of 99.999% lithium chloride, supra, in deionized water and let soak for one day. The tubing is then removed and placed into a fresh saturated solution of 99.999% lithium chloride and let soak for one day. The tubing is then installed in the sensor described in "Run #2" of U.S. Pat. No. 4,333,810. The sensor is preconditioned as taught in the U.S. Pat. No. 4,333,810 patent. The sensor is then exposed to a standard gas mixture containing 4 ppm chlorine gas and the response is about 8 millivolts. The sensor is used to estimate the chlorine gas concentration of samples over the next year and over this time is periodically recalibrated by exposure to standard gas mixtures including the 4 ppm chlorine gas standard. Over this one year time span the response of the sensor to the 4 ppm chlorine gas standard increases to about 40 millivolts.

EXAMPLE

The apparatus shown in FIG. 1 and described in the Detailed Description Of The Invention is constructed and the space 11 is filled with a saturated solution of 99.999% pure lithium chloride in deionized water The reservoir 9 is filled with a saturated solution of 99% pure lithium chloride, supra, in water. A voltage of 3 volts is applied to the platinum electrodes 12 and 14 using a Hewlett Packard direct current power supply 13. One day later the power supply 13 is turned off and the membrane 1 is removed from the tee 2 and the elbow 3 and a 1 inch long section is then installed in the sensor described in "Run #2" of U.S. Pat. No. 4,333,810. The sensor is preconditioned as taught in the U.S. Pat. No. 4,333,810 patent. The sensor is then exposed to a standard gas mixture containing 4 ppm chlorine gas and the response is about 40 millivolts. The sensor is used to estimate the chlorine gas concentration of samples over the next year and over this time is periodically recalibrated by exposure to standard gas mixtures including the 4 ppm chlorine gas standard. Over this one year time span the response of the sensor to the 4 ppm chlorine gas standard remains at about 40 millivolts. This example shows the advantage of the pretreatment method of the present invention relative to the Comparative Example above.

What is claimed is:

1. A method for constructing a sensor for chemical analysis comprising the steps of:
    partitioning a first aqueous electrolyte solution from a second aqueous electrolyte solution with a cation exchange membrane, the cation composition of the first solution being more than 99.99% of hydrogen and a single cation moiety selected from the group consisting of alkali metal cations and alkaline earth cations, the cation composition of the second solution consisting essentially of the same cation composition as the first solution;
    passing an electrical current sequentially through the first solution, through the membrane and then through the second solution so that the membrane is converted to the cation form of the first solution; and
    installing the membrane in a sensor for chemical analysis.

2. The method of claim 1 wherein the electrolyte of the first solution is lithium chloride.

3. The method of claim 1 wherein the membrane comprises a sulfonated fluorocarbon resin.

4. The method of claim 1 wherein the cation composition of the first solution is 99.999% or more of hydrogen ion and the single cation moiety.

5. The method of claim 2 wherein the first aqueous solution contains more than about 10 grams of lithium chloride per 100 grams of solution.

6. The method of claim 3 wherein the membrane is tubular in shape, the first solution contained in the bore of the tubular membrane.

7. The method of claim 6 further including recirculating the first solution through the bore of the tubular membrane during the step of passing an electrical current sequentially through the first solution, through the membrane and then through the second solution.

8. The method of claim 7 wherein the cation composition of the first solution is 99.995% or more of hydrogen ion and lithium ion.

9. The method of claim 8 wherein the sensor is the sensor described in Run #2 of U.S. Pat. No. 4,333,810.

* * * * *

UNITED STATES PATENT AND TRADEMARK OFFICE
CERTIFICATE OF CORRECTION

PATENT NO.   : 4,724,050

DATED        : February 9, 1988

INVENTOR(S)  : Sheryl M. Bergeron; Duane K. Wolcott

It is certified that error appears in the above-identified patent and that said Letters Patent is hereby corrected as shown below:

Col. 2, line 19, "oonnected" should read -- connected --;

line 20, "1/4 X 1/4" should read -- 1/8 X 1/4 --.

Col. 4, line 17, "oontaining" should read -- containing --.

Signed and Sealed this

Fifteenth Day of November, 1988

Attest:

DONALD J. QUIGG

*Attesting Officer*     *Commissioner of Patents and Trademarks*

UNITED STATES PATENT AND TRADEMARK OFFICE
CERTIFICATE OF CORRECTION

PATENT NO. : 4,724,050

DATED : February 9, 1988

INVENTOR(S) : Sheryl M. Bergeron and Duane K. Wolcott

It is certified that error appears in the above-identified patent and that said Letters Patent is hereby corrected as shown below:

Column 2, line 58, "negatively" should read -- positively --;

Column 2, line 60, "positively" should read -- negatively --;

Column 2, line 65, "positive" should read -- negative -- and "negative" should read -- positive --.

Signed and Sealed this

Twenty-eighth Day of February, 1989

Attest:

DONALD J. QUIGG

Attesting Officer    Commissioner of Patents and Trademarks